United States Patent [19]  
Intengan et al.

[11] Patent Number: 4,628,929  
[45] Date of Patent: Dec. 16, 1986

[54] RETRACTABLE BLADE BLEEDING TIME DEVICE

[75] Inventors: Franklin S. Intengan; Zindel H. Heller; Fred K. White, all of Miami, Fla.

[73] Assignee: American Hospital Supply Corporation, Evanston, Ill.

[21] Appl. No.: 766,878

[22] Filed: Aug. 16, 1985

[51] Int. Cl.⁴ ............................................. A61B 17/32
[52] U.S. Cl. ................................................... 128/314
[58] Field of Search .................... 128/314, 315, 329 R, 128/770

[56] References Cited

U.S. PATENT DOCUMENTS

| 55,620 | 6/1866 | Capewoll et al. | 128/314 |
|---|---|---|---|
| 580,969 | 4/1897 | Cohn | 30/272 R |
| 1,260,827 | 3/1918 | Stefanov | 42/86 |
| 1,572,191 | 2/1926 | Donnelly | 30/305 |
| 2,711,738 | 6/1955 | Koley et al. | 128/314 |
| 3,030,959 | 4/1962 | Gruner | 128/329 |
| 3,039,467 | 6/1962 | Stone et al. | 128/329 |
| 3,254,408 | 6/1966 | Hite | 30/189 |
| 3,712,293 | 1/1973 | Mielke | 128/26 |
| 3,762,416 | 10/1973 | Moss et al. | 128/305 |
| 3,902,475 | 9/1975 | Begg et al. | 128/2 R |
| 4,064,871 | 12/1977 | Reno | 128/26 |
| 4,078,552 | 3/1978 | Chen et al. | 128/26 |
| 4,157,086 | 1/1979 | Maiorano et al. | 128/637 |
| 4,539,988 | 9/1985 | Shirley et al. | 128/314 |
| 4,553,541 | 11/1985 | Burns | 128/314 |

FOREIGN PATENT DOCUMENTS 998838 6/1974 France .

OTHER PUBLICATIONS

Brochure "Surgicutt, an Important Advance in Bleeding Time Technique" and instruction sheet for Surgicutt of International Technidyne Corporation, Edison, N.J. 08820.

Primary Examiner—William R. Cline  
Assistant Examiner—Richard R. Cole  
Attorney, Agent, or Firm—Perman & Green

[57] ABSTRACT

A disposable device for making an incision in the skin of a human or animal by a retracting blade member that selfretracts after the incision is completed for bleeding time determinations, is disclosed. The device comprises a housing, a hammer mechanism pivotably positioned within the housing and including a cam surface, and a selfretracting shuttle supported within the housing and including a cam follower surface, the shuttle operative to travel in a vertical direction by (i) the movement of the cam surface along the cam follower surface and (ii) the force exerted on the shuttle by a first spring extending from the shuttle. Secured on the shuttle is a cutting surface {(blade(s)} operative to move out of the housing to make the incision and then selfretract into the housing. A second spring is operative to exert a force on the hammer to cause it (i) to move along the cam follower surface to cause the shuttle to travel downwardly thereby causing the blade to travel out of the housing and make the incision, and (ii) to move into a locked position to thereby secure the blade within the housing after the blade has retracted back into the housing due to force exerted by the first spring.

29 Claims, 9 Drawing Figures

RETRACTABLE BLADE BLEEDING TIME DEVICE

BACKGROUND OF THE INVENTION

I. Field of the Invention

This invention relates to a medical device useful in determining bleeding times, such as the time it takes for proper platelet aggregation to stop the free flow of blood, and more particularly, a single use, spring-loaded, disposable device for piercing the skin such as that of a human by employing a linear cutting edge transported by a moving carrier member in a direction substantially perpendicular to the skin to induce bleeding for carrying out bleeding time studies.

II. Description of the Prior Art

In the medical field it is a very common procedure, and often very necessary, to conduct a bleeding time test which measures the time required for the cessation of bleeding following a skin incision. This test is medically important because extended or prolonged bleeding time can be associated with, for example, a lack of or a great excess of platelets, abnormality of platelet function, coating of platelets by specific proteins or foreign materials or the action of certain drugs; e.g., aspirin.

Although the bleeding time test procedure was first described about seventy-five years ago, it did not receive general acceptance until the 1940's at which time the test's sensitivity was increased by making a skin incision on the forearm of the patient while maintaining a blood pressure cuff inflation of 40 mm Hg. Using this procedure, a technologist simultaneously starts a stop watch while making the incision. The emerging blood is then gently blotted every 30 seconds. The cessation of bleeding is defined as the time at which the blotting paper is no longer stained by the emerging board. This amount of time is generally recorded to the nearest half-minute.

U.S. Pat. No. 4,078,552 describes a prior art device that is used for making standard and reproducible skin punctures in a patient to determine bleeding time. The device comprises a housing, a spring-loaded blade shuttle, means for restraining the blade shuttle and means for irretrievable release of the blade shuttle to effect incision of the patient's skin through a slit opening in the housing. The direction of travel of the blade shuttle is perpendicular to the patient's skin and the cutting edge of the blade is described as linear.

The present invention is distinguished, in part, such as from the aforementioned U.S. Pat. No. 4,078,552, by the physical separation of the spring-loaded drive mechanism from the blade-shuttle, which is separately mounted and free to move totally independently therefrom. This separation enables implementation of the retraction feature described below.

On actuation, the spring transfers its stored energy to a first moving member, called the hammer, which then transfers its energy to the semi-freely mounted shuttle by a glancing percussive action, thereby imparting an energetic motion to the shuttle towards the skin, and especially the blade mounted thereon, which is guided in its tracks to exit the housing and impact the skin. Following the percussive action, the hammer and shuttle are completely disengaged. The hammer travels to its final rest position to receive and lock a mating portion of the shuttle. The shuttle recoils to return into the housing from its exposed, incising position by a moderately-forceful, integral, leaf spring to latch that member in its locked or latched position. In this position, the shuttle and blade are safely latched out of the way of potential contact with any personnel, including the patient, thereby reducing opportunity for laceration or infection of medical personnel, visitors or other patients. Because the blade is latched up into the housing after use of the device, no special handling precautions need be used for safe disposal of the device.

The device described by the present invention has been measured by a "Ballistic Pendulum" type of device to be approximately 10 millijoules. The device described in U.S. Pat. No. 4,078,552 delivers about 1.7 millijoules. One reason that the device of the present invention must deliver more energy is that it does not have the luxury of relying on the restoration of the skin pressure against the blade to complete the incision process, as the device of the '552 patent does. The blade retracts so fast in the device of the present invention that it is effectively disengaged from the skin before the latter undergoes significant deformation. Furthermore, due to the design of the housing portion where the blade extends from the housing, the skin is stretched taut for easier penetration of the blade therethrough.

Conversely, the skin in the '552 device aids in the penetration of the blade since skin is hard and is tough to cut. The underlying tissue is spongy like gelatine and, under inward deformation, exerts a hydrostatic outward restoring force on the skin. Therefore, on the '552 device whose blade remains extended, the restoring force of the skin will continue the incision from the points of initial impact such at the blade ends. In the present device, because the blade moves through its cycle so quickly, it must rely totally on speed of penetration to complete the incision for the length of the cutting edge before the skin recoils from impact.

Another distinguishing feature over the '552 patent is the orientation of the blade on the shuttle such that, although the direction of travel is perpendicular to the skin, the cutting edge enters the skin at an angle of approximately five degrees from parallel. This makes for a unique slicing action caused by greater concentration of shear stress at the leading point of contact so that a lancet-type incision is made followed by extended shearing action as the blade edge penetrates to the position of maximum extension. The great speed of the present device also seems to be associated with reported reduction of sensation of pain. It is believed that the blade is retracted from the skin before nerve impulses can reach the brain.

Although the prior art does describe different types of devices for making skin incisions in a patient to determine bleeding time, none of these devices seem to have the combined advantage of reliability, ease of handling reproducibility, prevention of the formation of a scar in the patient, safety, speed of use, avoiding infection in the patient and minimizing pain to the patient.

SUMMARY OF THE INVENTION

It is therefore a primary object of the present invention to overcome many of the disadvantages of the incision making devices described by the prior art and provide a simple, disposable device for making incisions in a patient's skin that are reproducible incisions of a controllable length and depth to obtain accurate bleeding time determinations.

It is a further object of the present invention to provide a device for making incisions in a patient's skin which is very easy to operate, and performs its function very quickly.

It is a further object of the present invention to provide a device for making incisions in a patient's skin which is a single use device and can be safely disposed of after use without special handling precautions.

It is a further object of the present invention to provide a device for making incisions in a patient's skin which avoids the very great hazard of causing an infection in the patient.

It is still a further object of the present invention to provide a device for making incisions in a patient's skin which device is extremely safe to use, provides a unique means to selfretract its blade back into the device's housing after use and a means to totally prevent the blade from emerging from it housing after use despite rough handling. This means further prevents reuse of the device.

It is still a further object of the present invention to provide a device for making incisions in a patient's skin which minimizes the pain to the patient and avoids leaving the patient with a scar.

These and other beneficial objects and advantages are achieved in accordance with the present invention by providing a disposable device for making an incision in the skin such as that of a human by a retracting blade member that selfretracts after the incision is completed, The device comprises a housing, a hammer means pivotably positioned within the housing and including a cam surface and a selfretracting shuttle means supported within the housing and including a cam follower surface, the shuttle means being operative to travel in a substantially vertical (up and down) direction due to (i) the movement of the hammer cam surface along the cam follower surface and (ii) the force exerted on the shuttle means by a first spring means that extends from the shuttle means. Included is a blade means that is secured to the shuttle means and operative to move out of the housing to make the incision and then selfretract back into the housing. A second spring means is included to exert a force on the hammer means to cause it (i) to move along the cam follower surface to cause the shuttle means to travel downwardly thereby causing the blade to travel out of the housing and make its incision, and (ii) to move into a locked position to thereby secure the blade within the housing after the blade has retracted back into the housing due to the force exerted by the first spring means.

The shuttle means is structured to have positioned thereon one or two blades which travel to the skin perpendicularly. When two blades are used they are preferably positioned on the shuttle means to be mirror images of each other. In fact, they are positioned on the shuttle means such that each of the incisions that they produce in the skin begins to bleed at substantially the same time. Furthermore, whether using one or two blades for making the incision(s), each blade can be positioned on the shuttle means such that the length of the blade strikes the skin of the patient at an angle to the skin. This angle is preferably about 5° plus or minus ½°.

The disposable bleeding time device in accordance with the feature of the present invention greatly facilitates performance of the bleeding time test on patients by controlling both the depth and length of the cut. The device is designed to produce incisions that are a nominal 5 mm in length and 1 mm deep.

The sturdy, ultrasonically sealed case of the bleeding time device has a tear-away tab to guard against premature release of the blade. A safety mechanism automatically retracts both the trigger and blade into the casing after use of the device. Once utilized, the blade(s) remain(s) permanently retracted to eliminate accidental cuts with possible transfer of hazardous pathogens. The device is sterilized, used once and then discarded.

BRIEF DESCRIPTION OF THE DRAWINGS

For a better understanding of the invention as well as other objects and further features thereof, reference is made to the following detailed disclosure of this invention taken in conjunction with the accompanying drawings wherein.

DETAILED DESCRIPTION OF THE PREFERRED EMBODIMENTS

Figure 1:
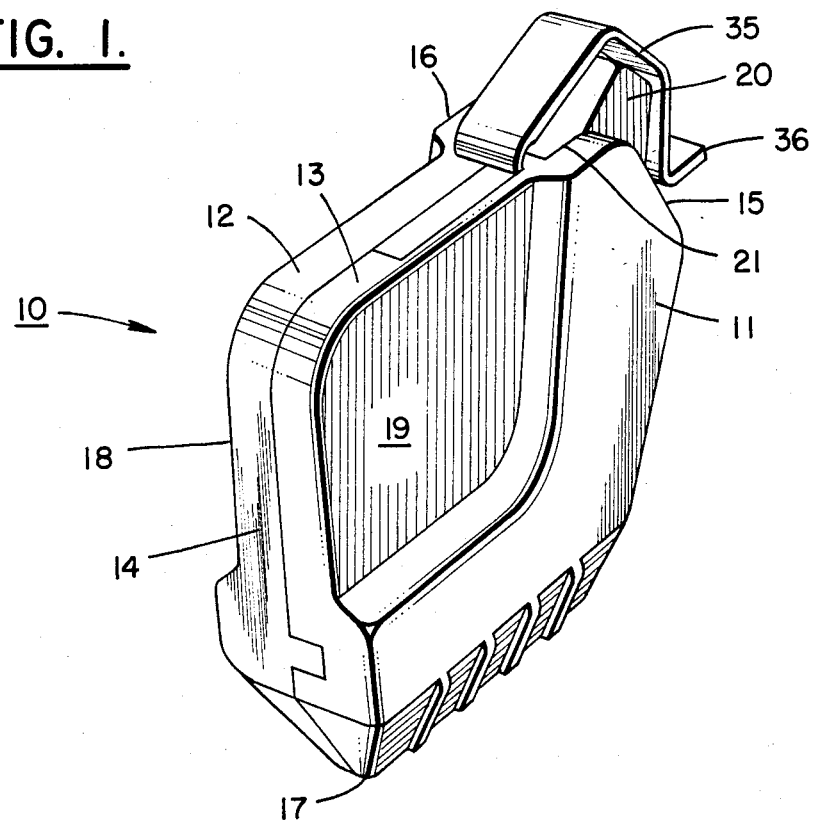
FIG. 1 is a perspective view of a disposable device for making an incision in an animal or human by a retracting blade member in accordance with the features of the present invention.

Reference is now made to the drawings wherein a disposable device for making an incision in the skin such as that of a human by a retracting blade member that travels perpendicularly to the skin to make an incision and then selfretracts after the incision is completed for bleeding time determinations is illustrated in detail. Referring to FIG. 1, it can be seen that the device 10 in accordance with the present invention comprises a hollow housing 11 that is formed of two plate members 12 and 13 which are secured together. The housing including front and rear surfaces 14 and 15, top and bottom surfaces 16 and 17, and side surfaces 18 and 19 defined by the face portion of each of plate members 12 and 13. Also shown is a pivotable trigger member 20 extending through opening 21 in the top portion of housing 11, the trigger member being the mechanism by which the users of the device place their fingers to the device and apply a pushing force thereto to activate the device.

As more clearly shown in FIG. 2, device 10 is formed of two plate members 12 and 13 that are secured together to support all of the components therein in a functioning manner by inserting each of post members 22 extending from plate 13 into their respective mating openings 23 located in plate 12. The device utilizes the toggle and cam principle for the actuation of its mechanism and further introduces a retracting blade member that selfretracts after the stroke of the incision is completed. To achieve this goal the housing is equipped with a hammer means 24, which is initially set at toggle position, including a cam surface 25 and notch 26, and a self-retracting shuttle means 27 carrying a blade 28. The shuttle means 27 is provided with a cam follower surface 29 which helps to urge a quick or snap motion of a precise stroke to the blade when hit by the cam surface 25 when the hammer is released from toggle position.

Hammer means 24 is pivotally mounted within the housing via posts 30 that are inserted within openings 31 (only one shown) positioned on the housing. The device in accordance with the features of the present invention functions as described hereinbelow due to the biasing forces exerted retraction by spring 32 in the form of a leaf spring extending from shuttle means 27, and by the biasing forces exerted on the hammer means due to drive or power spring 33 that rides along spring guide 34 that extends from the hammer means.

As more fully described below, two unique features of the present invention include (i) the hammer mechanism which activates the blade shuttle on the incision stroke, and (ii) the leaf spring attached to the shuttle which causes retraction of the blade into the housing after the incision has been made. These features prevent the reuse of the device and the inadvertant contact of an exposed blade with either the patient or the medical personnel at time of disposal.

Figure 3:
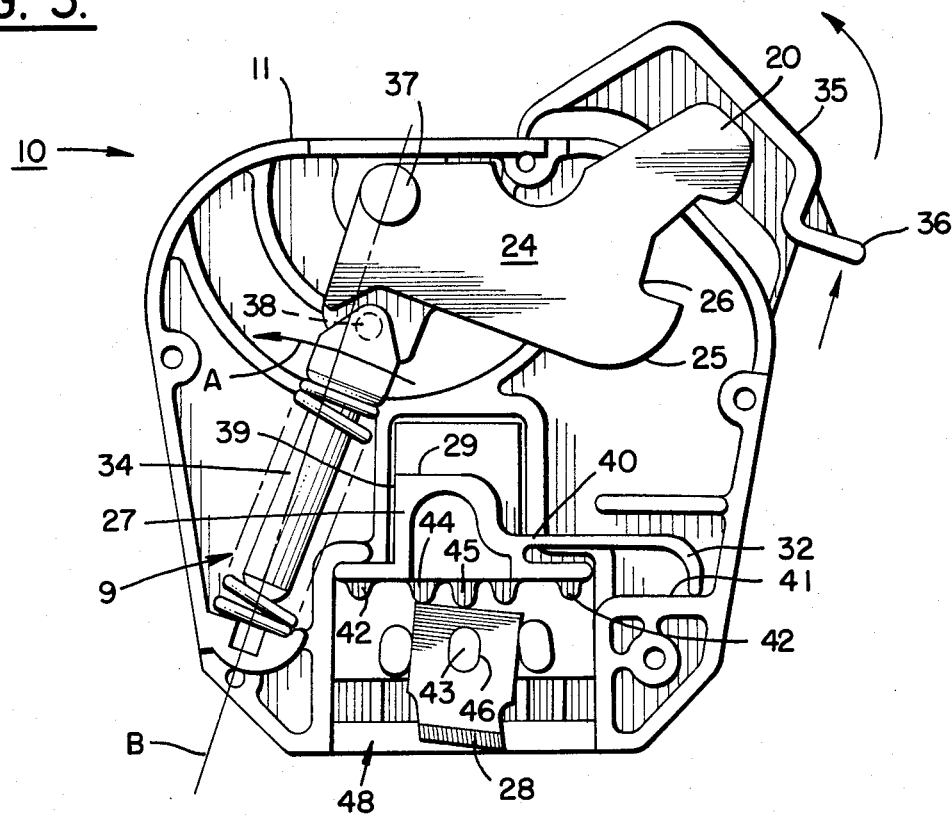
FIG. 3 is a side elevational plan view of the device of FIG. 1 with the perspective shield in place and the cover plate removed to illustrated the interior features of the device.
Figure 4:
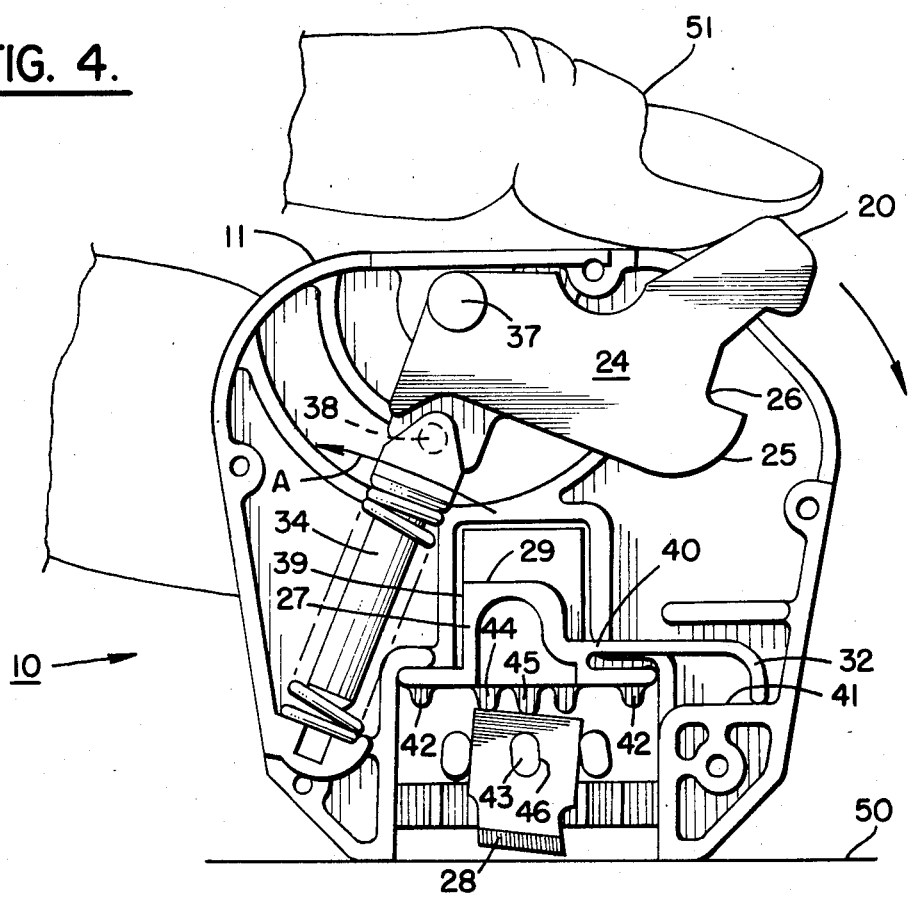
FIG. 4 is a side elevational plan view of the device of FIG. 1 with the cover plate removed and the user's finger in place on the trigger mechanism ready to use the device.

FIG. 3 illustrates all of the basic features of the device 10 in accordance with the present invention positioned at such time when the device is first removed from its sealed package and ready for use. To prevent accidental forces from being exerted on the trigger mechanism 20, a protective shield 35 is positioned over the trigger and is preferably not removed (by pulling on the tab 36) until the device is ready to be used. In fact after removing the protective shield, the device should then be placed on the skin of the patient and the trigger pushed by the user's finger in the manner as illustrated in FIG. 4.

The trigger mechanism 20 is an integral part of hammer means 24 which is pivotably mounted to housing 11 at locating 37. Hammer means 24 includes a notch 26, cam surface 25 and a pivotable connection 38. The lower end of spring 33 is seated within the housing at seating area 9 so that as the hammer means 24 moves clockwise, the spring 33 and guide 34 will be carried to the left about the seating area. However, as the hammer means approaches its ultimate latched position; that is, its furthest position in the clockwise direction, the bottom portion of spring guide 34 is carried away from seating area 9 while spring 33 remains seated therein.

Pivotable connection 38 moves with the hammer means to carry the head portion of the spring guide member 34 in the counterclockwise direction, or to the left, as shown by arrow A. Prior to actuation of the trigger portion of the hammer means, the biasing force to be exerted on the hammer means by the head portion of spring guide member 34 tends to keep the hammer in its cocked or original position. This is because pivotable connection 38 is to the right of reference line B, a line running between hammer location 37 and the approximate centerline of seating area 9. As the trigger is depressed, pivotable connection 38 moves eventually to the left of the reference line B and spring 33 biases the hammer means 24 further in the clockwise direction.

Shuttle means 27 travels towards the skin and may, for instance, move in a substantially vertical manner within the housing. Shuttle means 27 is preferably formed of an integral one piece member which is capable of riding vertically along channel 39. It includes a spring member 32 capable of providing a biasing force which will return the shuttle to its retracted position except during the power stroke. The spring member 32 is preferably in the form of a leaf spring extending from the shuttle at one end portion 40 thereof and contacting a surface 41 of housing 11 to provide a biasing force (an upward force on the shuttle) as the shuttle is moved in a downward direction.

The top portion of the shuttle includes a cam follower surface 29 which directs the movement of cam follower 25 as described hereinbelow. Extending from the shuttle are a plurality of bosses or support members 42 which assist in properly securing and positioning blade 28 to the shuttle. In the particular embodiment shown in FIGS. 3–6, a single blade is used for making the incision. The blade is illustrated as being secured to the shuttle by boss 43 and properly positioned thereon by bosses 44 and 45. The blade includes a mounting hole 46 in its center which enables it to be placed over boss 43, and the boss subsequently ultrasonically staked thereto to make a rivet-like connection of the blade to the shuttle.

It was found in accordance with a preferred embodiment of the present invention that the use of certain blade angles had unexpected advantages over certain devices described in the prior art for making an incision in the skin of the patient. In one embodiment of the present invention the blade or blades (see the two-blade embodiment described hereinbelow) can be brought down to the skin of the patient with the lower point of the blade striking the skin first, exerting maximum pressure to initiate puncture of the skin. Then, as the blade travels perpendicularly to the skin, the edge exerts maximum shearing force along the direction of the incision, to produce a slice rather than a chop.

The preferred angle of the blade at its bottom as measured relative to the skin (or alternatively the bottom of the device) is preferably 5° plus or minus ¼°. By providing a slicing rather than a chopping action to the skin, there is generally less trauma to the skin area about the incision. Because of this it is believed that there is much less possibility of leaving a scar after the incision heals.

The housing 11 includes element or surface 47 which acts as a stop mechanism with regard to shuttle 27 in its downward movement in channel 39 to thereby only allow blade 28 to travel a specific distance out of housing 11 through opening 48 located in the bottom portion of the housing to make the incision. Shoulder means 7 on the shuttle means 27 (see in FIG. 2b) strikes stop surface 47 to limit the shuttle's (and blade's) travel in the direction towards the skin.

One important feature of the device in accordance with the present invention is that the part of the blade cycle wherein the blade is exposed out of (below the bottom surface of) housing 11 is of a very short duration. It is estimated that the blade is energed from the housing for a total amount of time (including time to make the incision and retract) of about 20 microseconds. Another important feature of the device in accordance with the present invention is the reproducibility of the incision to assure that the blood timing test is accurate. In the medical field this is called the "standard cut". The standard cut is normaly about one millimeter deep and about five millimeters long.

Figure 5:
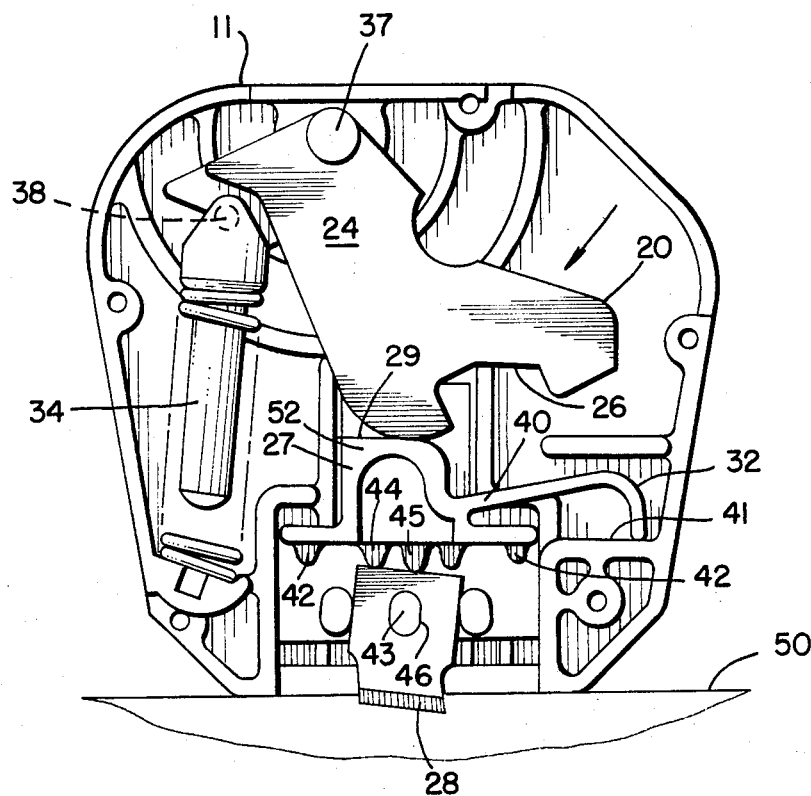
FIG. 5 is a side elevational plan view of the device of FIG. 1 with the cover plate removed illustrating the position of the major components of the device during the time the incision is being made in the patient's skin.
Figure 6:
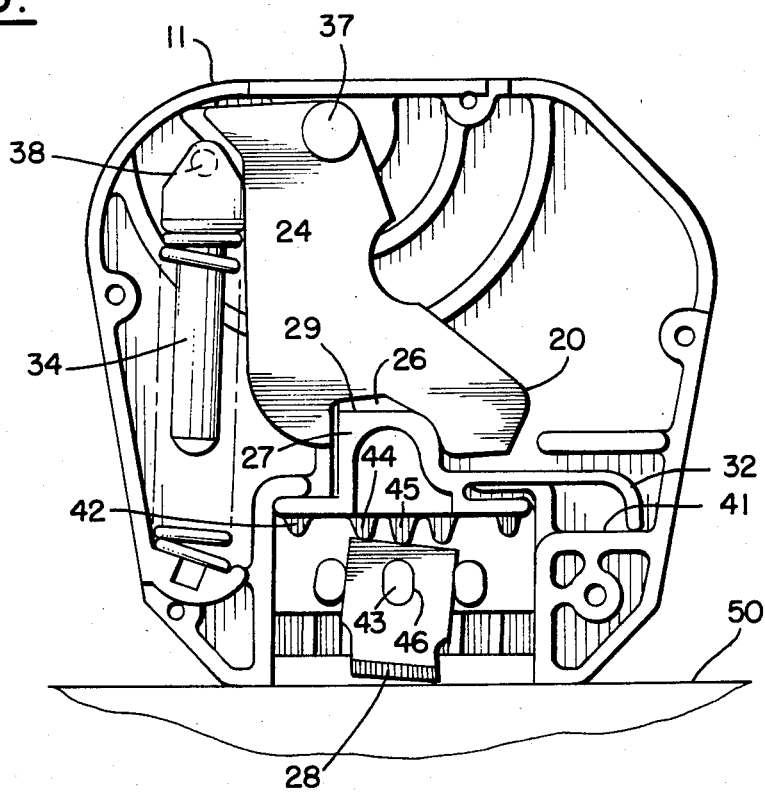
FIG. 6 is a side elevational plan view of the device of FIG. 1 with the cover plate removed illustrating the position of the major components of the device after the incision has been made and the blade has selfretracted back into the housing.

There is illustrated in FIGS. 4–6 the operation of the device in accordance with the preferred features of the present invention. When it is desired to use device 10, it is removed from its sealed package, the protective shield is removed as a cover for the trigger mechanism and the device is placed against a subject (such as against the arm) with the slot or opening 48 making contact with the subject's skin 50 so that the line of action of the blade may be approximately perpendicular to the skin where it is desired to make an incision. The device is now armed and ready for use by the user 51 pushing on the trigger mechanism 20 as shown in FIG. 4.

As the trigger mechanism is pushed by the user, the hammer 24 wil rotate in the clockwise direction shown by the arrow and reach a position where the biasing force on the hammer (caused by the force that drive spring 33 exerts on the head portion of spring guide 34) actually causes the hammer to go through the center position (to the left of reference line B) and urges the hammer further in a clockwise direction. Mechanically, the hammer can be described as an "over the top dead center toggle position device". Once the trigger of the hammer is activated by the user and the pivotable connection 38 passes the top dead center position, the force caused by spring 33 actually helps accellerate the hammer's movement to its full position in a clockwise direction. In fact, once the hammer has reached the position where spring 33 begins to urge it further, the hammer completes its movement extremely fast.

As shown in FIG. 5, as the hammer 24 rotates in a clockwise direction due to the biasing force exerted by spring 33, cam surface 25 makes contact with and rides along cam follower surface 29 located on the top portion of shuttle 27. This motion then moves the shuttle towards the skin, such as in a downward direction, causing blade 28 to move out of or extend from the housing through opening 48 and make the incision in the subject's skin.

Figure 2A:
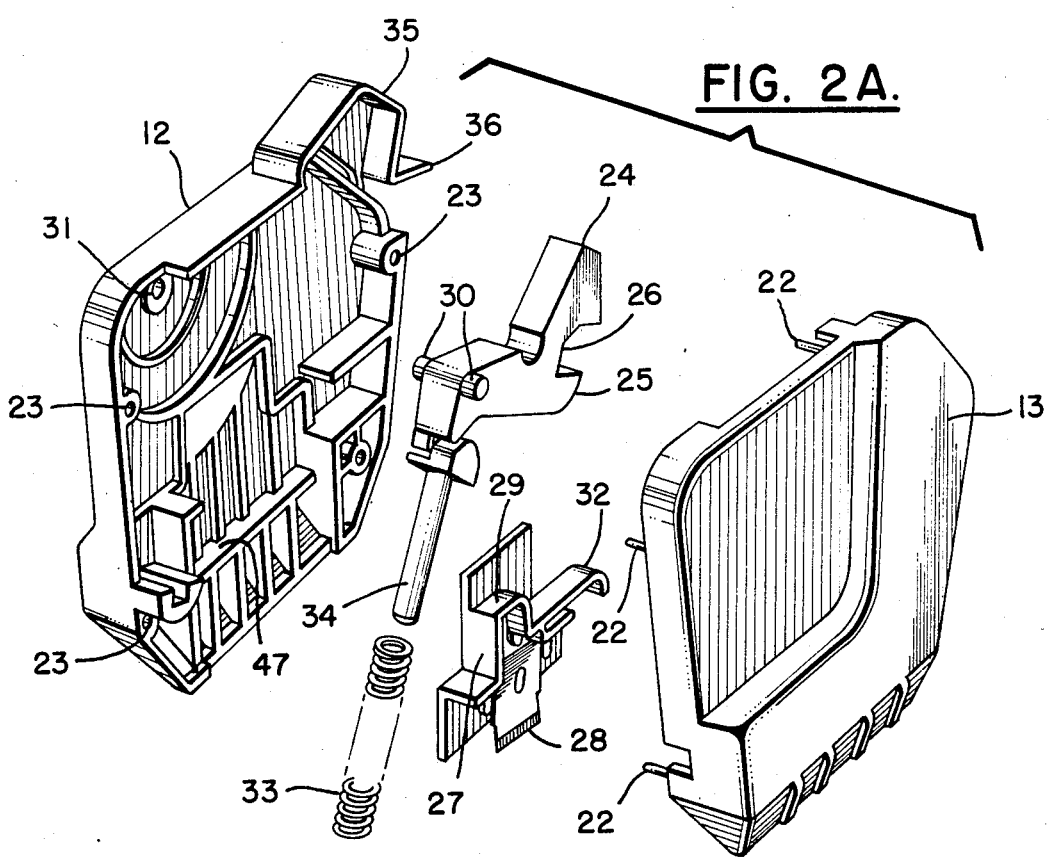
FIG. 2a is a perspective view of some of the significant parts of the device of FIG. 1, illustrated in a disassembled manner.
Figure 2B:
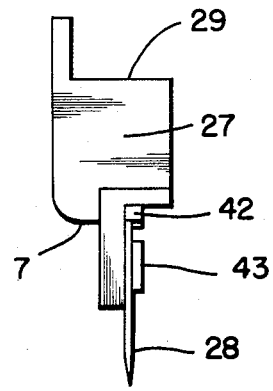
FIG. 2b is an end view of the shuttle means of FIG. 2a showing the shoulder surface thereon for stopping the movement of the shuttle means in the direction that projects the blade(s) from the housing and into the skin.

Extending from the shuttle is a leaf spring 32 which is positioned at its end portion on a surface 41 of housing 11 in a manner such that as shuttle 27 moves in downward direction, the leaf spring causes an increasing biasing force on the shuttle (and blade) in an upward direction. This upward biasing force in the device in accordance with the present invention is at its maximum at such time in the operation of the device when the shuttle has been pushed vertically downward to stop surface 47, which is an integral part of the housing half (see FIG. 2) and blade 28 has completed making its incision in the skin. As shown in FIG. 2a, shuttle means 27 has a surface which bottoms out on stop surface 47 during its downward motion.

After the time the shoulder surface 7 bottoms on stop surface 47, the biasing force of the leaf spring causes the shuttle to move in an upward direction causing retraction of the blade into the housing 11. As shown in FIG. 6, the combined biasing forces of spring 33 and leaf spring 32 help to complete the hammer means clockwise movement to its full position in a clockwise direction. In this position of the hammer, the blade is totally retracted and the hammer is locked onto the shuttle thereby locking the shuttle and blade combination in its retracted position. Thus, once the device has been triggered (used), there is no chance for the blade to emerge or extend from the housing again despite rough handling due to its latched condition. Also, this prevents reuse of the device. The locking effect is achieved by the end portion or corner 52 of shuttle 27 positioning itself within notch 26 of hammer means 24.

The device 10, once assembled, is sterilized preferably with ethylene oxide. Because of this, the plastic materials used in the device cannot react to the sterilization process or other chemical exposure, nor swell. Thus, a number of the elements in the device are preferably made of a plastic material such as "Celcon", a smooth, chemically-inert plastic made by the Celanese Corporation. The choice of this material is very important because of its mass, its relatively low surface friction, its immunity to the stresses engendered by the ultrasonic bonding of the housing, its ability to stand up under the sterilizing process and its basic springness. The housing is ultrasonically bonded all around its outer edge. The housing is preferably made of a high impact styrene.

The shuttle 27, spring guide 34, hammer 24, and leaf spring 32 on the shuttle are all preferably made of Celcon.

The design of leaf spring 32 is, of course, very important to its providing the necessary biasing force to operate the device. The spring has been designed to be strong enough to return the shuttle 27 and to absorb the force of the hammer means 24, but weak enough so as not to appreciably resist the downward power stroke. To achieve this end purpose in a device such as described herein the leaf spring is preferably made of a material such as Celcon having a thickness of about 0.025 inches and a width of about 0.120 inches.

The shuttle 27 is a one-piece or integral element and includes the leaf spring 32 portion. The blade 28 is mounted on the shuttle. The blade has a mounting hole in its center which is placed over the boss on the shuttle and the boss ultrasonically staked thereto to make a rivet-like connection to the blade. The blade employed in the device is preferably one made of magnetic stainless steel and can be the standard stock used in razor blades. Razor blades formed of a stainless steel alloy such as a low carbon stainless steel similar to 440A used in U.S. stainless steel instruments and shaving blades and identified by mill spec MS #23-0000-0109 are preferred. In one possible embodiment the blade can contain three bevels. The plane nearest the point of the blade being about 10° which is stepped to a plane of about 8° and finally to a third plane of about 6°.

Figure 7:
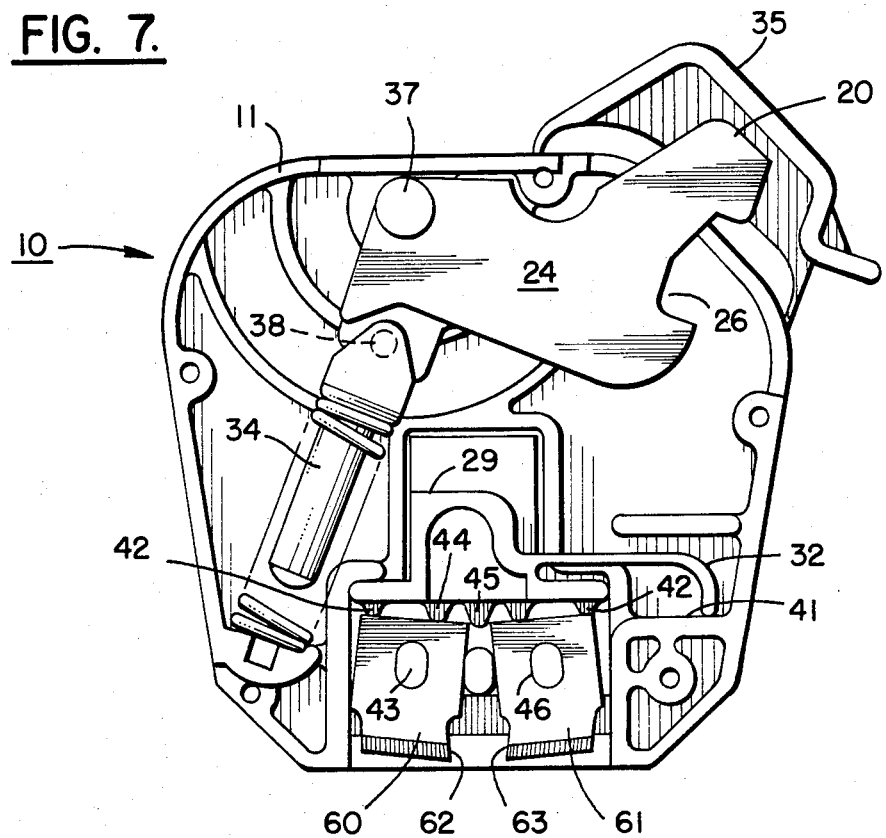
FIG. 7 is a side elevational plan view of the device in accordance with another feature of the present invention with two blades, the device having the protective shield in place and the cover plate removed to illustrate the interior features of the device.

Another embodiment of the device for making an incision in accordance with the features of the present invention, is one having two blades 60 and 61, as shown in FIG. 7, for making two simultaneous incisions. The two blade version of the device 10 shows the points 62 and 63 of each blade close together, the blades preferably being mirror images of each other. This allows one to use one set of tooling to manufacture the shuttle. However, the blades can be placed so that their points are at opposite ends or the points are set in the same fashion. It is also preferable to keep the points of the each of the two blades in proximity (as shown in FIG.

7) so that they each are in the same area of the skin and their incisions begin to bleed at the same time and in the same manner even if the housing is set on the skin with the housing slightly tilted in the force-and aft direction. Other than the number of blades and the way they are ultrasonically staked by the bosses on the shuttle, the rest of the mechanism is precisely the same for either the one blade or the two blade version.

In the single blade device in accordance with the present invention, the blade is mounted on a Celcon boss and ultrasonic energy and pressure is applied to the boss to stake the boss to the blade. The boss becomes molten and flows around and fills the hole in the blade. When it solidifies, it holds the blade in place firmly. The ultrasonic staking of the blade to the shuttle is done separately from the ultrasonic staking of the housing members together. In the two blade version, the two outer bosses in the shuttle are inserted into the holes in the blades (see FIG. 7) and they are ultrasonically staked. During this ultrasonic staking process, the middle boss is also made to flow and it flows in such a manner so as to fill the space between the two blades and form a support surface for the blades so that the blades are further held in place in the shuttle.

Figure 8:
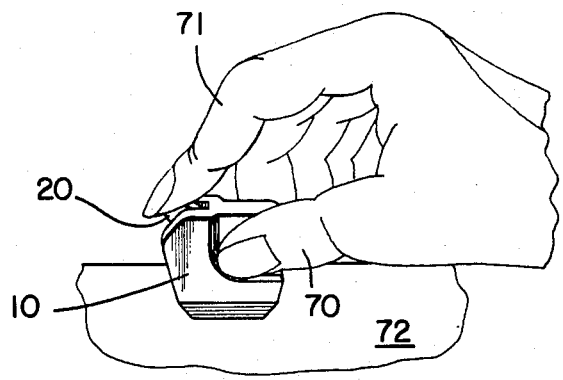
FIG. 8 is a side plan view of a device in accordance with the features of the present invention positioned on a patient's arm and ready for use.

A step-by-step example of how the device in accordance with the present invention can be used on a human patient in a medical procedure for making an incision for bleeding time determination, is as follows:

1. First a sphygmomanometer cuff is loosely paced on the patient's arm.
2. An area is selected, free of visible surface veins, on the volar forearm about five (5) inches below the patient's elbow bend. The site is cleaned with alcohol and then wiped dry with a dry sterile material.
3. A sealed unit in accordance with the present invention is removed from its box and its sealed bag. The protective plastic tab located over the trigger mechanism is then broken away.
4. The cuff is inflated to about 40 mm. Hg and maintained at this pressure level throughout the measurement.
5. The device 10 for making an incision in accordance with this invention and as shown in FIG. 8 is held firmly between the users thumb 70 and middle finger 71 while positioning the device against the incision site on the patient's arm 72. The device should preferably be oriented perpendicular to the site of the incision. Furthermore, device 10 should be seated against the incision site until the four bottom corners of the device are just touching the skin and opening 48 is directly over the skin.
6. The trigger 20 of the device is then pushed forward with the user's index finger while maintaining the perpendicular orientation and proper pressure. As described hereinabove, this action will cause the spring-loaded blade means to release during the forward motion of the trigger and retract when the trigger is no longer visible. The device is then removed from the incision site and the timer is started.
7. The edge of a filter paper is then used to blot blood near the edge of the incision at thirty (30) second intervals. This step is repeated at thirty (30) second intervals until blood stains cease to form on the filter paper. The filter paper is preferrably sprayed with a fixative after use. The bleeding time is recorded to the nearest thirty (30) second interval.
8. When the specific embodiment of the device in accordance with this invention that employs two blades is used to make two incisions on the patient's arm, the same procedure as described above is used. To obtain the bleeding time, the user obtains the average bleeding time of the two incisions to the nearest thrity (30) second interval.
9. The used device is then discarded.

While this invention has been described in conjunction with specific embodiments thereof, it is evident that many alternatives, modifications and variations will be apparent to those skilled in the art. Accordingly, the present invention is intended to embrace all such alternatives, modifications and variations, and fall within the spirit and scope of the appended claims.

We claim:

1. A disposable device for making an incision in the skin such as in a human by a retracting blade member that selfretracts after the incision is completed for bleeding time determinations comprising:
   a housing which inclues a blade opening;
   hammer means pivotably positioned within the housing and including a cam surface;
   selfretracting shuttle means supported within the housing and including a cam follower surface, the shuttle means operative to travel towards the skin by (i) the movement of the cam surface along the cam follower surface and (ii) the biasing force exerted on the shuttle means by a first spring means extending from the shuttle means;
   blade means secured to the shuttle means and operative to extend through said opening out of said housing to make the incision and then selfretract into the housing; and
   second spring means operative to exert a force on the hammer means to cause it (i) to travel along the cam follower surface to cause the shuttle means to travel towards said opening thereby causing the blade to travel out of the housing and make the incision and, (ii) to travel into a locked position to thereby secure the blade within the housing after the blade has retracted back into the housing due to force exerted by the first spring means.

2. The device according to claim 1 further comprising a trigger means located on said hammer means for allowing a user to actuate the device.

3. The device according to claim 2 wherein said trigger device is actuated by a force exerted thereon releasing said hammer means to be driven along said cam follower surface by said spring means.

4. The device according to claim 1 wherein said hammer means includes a notch positioned thereon capable of causing said hammer means to lock onto said shuttle means after said cam surface travels along said cam follower surface.

5. The device according to claim 1 further comprising a spring guide means for positioning said second spring means.

6. The device according to claim 5 wherein said spring guide means includes a head member operative to transfer the force exerted by said second spring to said hammer means.

7. The device according to claim 6 wherein said head member is pivotably mounted to said hammer means.

8. The device according to claim 1 wherein said shuttle means includes a plurality of support members operative to position and support said blade means on said shuttle means.

9. The device according to claim 8 wherein said shuttle means, first spring means and support members are formed of an integral element.

10. The device according to claim 8 wherein said blade means includes an opening for inserting a support member therein and securing said blade means to said shuttle means.

11. The device according to claim 8 wherein said support member is ultrasonically staked to secure said blade means to said shuttle means.

12. The device according to claim 1 wherein said first spring means is a leaf spring extending at one end from said shuttle means and supported at its other end by said housing whereby movement of said shuttle means towards the skin causes the leaf spring to exert an upward biasing force on said shuttle means.

13. The device according to claim 1 further comprising a shielding means operative to be secured to said housing and protectively cover said trigger means.

14. The device according to claim 1 further comprising the stop means positioned on said housing and operative to limit the downward movement of said shuttle means towards the skin.

15. The device according to claim 1 wherein said blade means comprises one blade.

16. The device according to claim 1 wherein said blade means comprises two blades.

17. The device according to claim 16 wherein said blades are positioned on said shuttle means such that each of said incisions on said skin by each of said blades begins to bleed at substantially the same time.

18. The device according to claim 1 wherein said blade means is positioned on said shuttle means such that the length of the blade strikes said skin at an angle to said skin.

19. The device according to claim 18 wherein said angle is about 5 degrees plus or minus ½ degree.

20. The device according to claim 18 wherein said blade means comprises one blade member.

21. The device according to claim 18 wherein said blade means comprises two blades, each blade striking said skin at an angle to said skin.

22. The device according to claim 21 wherein the blades are mirror images of each other.

23. The device according to claim 21 wherein each of said blades is at an angle of 5 degrees plus or minus ½ degree to said skin.

24. The device according to claim 21 wherein said blades are positioned on said shuttle means such that each of said incisions on said skin by each of said blades begins to bleed at substantially the same time.

25. A disposable device for making an incision in the skin such as in a human by a retracting blade member that selfretracts after the incision is completed for bleeding time determinations comprising:
   a housing which includes a blade opening;
   hammer means pivotably positioned within the housing and including a cam surface;
   selfretracting shuttle means supported within the housing and including a cam follower surface, the shuttle means operative to travel towards the skin by (i) the movement of the cam surface along the cam follower surface and (ii) the biasing force exerted on the shuttle means by a first spring means extending from the shuttle means;
   at least one blade secured to the shuttle means and operative to extend through said opening out of said housing to make at least one incision and then selfretract into the housing, each blade positioned on the shuttle means such that the length of the blade strikes the skin at an angle to the skin; and
   second spring means operative to exert a force on the hammer means to cause it (i) to travel along the cam follower surface to cause the shuttle means to travel towards said opening thereby causing each blade to travel out of the housing and make its incision, and (ii) to travel into a locked position to thereby secure each blade within the housing after each blade has retracted back into the housing due to the force exerted by the first spring means.

26. The device according to claim 25 wherein said angle is about 5 degrees plus or minus ½ degree.

27. The device according to claim 25 wherein there are two blades secured to the shuttle means.

28. The device according to claim 27 wherein the blades are mirror images of each other.

29. The device according to claim 27 wherein said blades are positioned on said shuttle means such that each of said incisions on said skin by each of said begin to bleed at substantially the same time.

* * * * *